(12) United States Patent
Zhu et al.

(10) Patent No.: US 12,239,521 B2
(45) Date of Patent: Mar. 4, 2025

(54) SUTURE-FREE COAGULATION-ASSISTED FIXED CARDIAC PATCH AND PREPARATION METHOD THEREOF

(71) Applicant: ZHEJIANG UNIVERSITY, Hangzhou (CN)

(72) Inventors: Yang Zhu, Hangzhou (CN); Yuwen Lu, Hangzhou (CN); Changyou Gao, Hangzhou (CN); Tanchen Ren, Hangzhou (CN); Liyin Shen, Hangzhou (CN); Xiaoqian Hong, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 18/695,835

(22) PCT Filed: Aug. 2, 2022

(86) PCT No.: PCT/CN2022/109644
§ 371 (c)(1),
(2) Date: Mar. 27, 2024

(87) PCT Pub. No.: WO2023/045568
PCT Pub. Date: Mar. 30, 2023

(65) Prior Publication Data
US 2024/0335272 A1  Oct. 10, 2024

(30) Foreign Application Priority Data
Sep. 27, 2021  (CN) .......................... 202111133190.0

(51) Int. Cl.
*A61F 2/00* (2006.01)
*A61F 2/08* (2006.01)

(52) U.S. Cl.
CPC .......... *A61F 2/0063* (2013.01); *A61F 2/0811* (2013.01); *A61F 2002/0817* (2013.01); *A61F 2002/0847* (2013.01)

(58) Field of Classification Search
None
See application file for complete search history.

(56) References Cited

U.S. PATENT DOCUMENTS

| 2003/0082148 A1 | 5/2003 | Ludwig et al. |
| 2014/0228867 A1 | 8/2014 | Thomas et al. |

FOREIGN PATENT DOCUMENTS

| CN | 103874465 A | 6/2014 |
| CN | 111467575 A | 7/2020 |

(Continued)

OTHER PUBLICATIONS

Kazuro L. Fujimoto, et al., An Elastic, Biodegradable Cardiac Patch Induces Contractile Smooth Muscle and Improves Cardiac Remodeling and Function in Subacute Myocardial Infarction, J Am Coll Cardiol., 2007, pp. 1-15, vol. 49, No. 23.

(Continued)

*Primary Examiner* — Farah Taufiq
(74) *Attorney, Agent, or Firm* — Bayramoglu Law Offices LLC

(57) ABSTRACT

A suture-free coagulation-assisted fixed cardiac patch and fabrication method thereof are provided. The cardiac patch includes a polymeric procoagulant base and a barbed microneedle fixed on the polymeric procoagulant base, and a side surface of the polymeric procoagulant base with the microneedle has a microporous structure which does not penetrate the solid base of the polymer; an included angle α between the microneedle and the plane where the polymeric procoagulant base located is 60-90°, and the microneedles are evenly distributed on the polymeric procoagulant base at a density of 5-50 threads/cm2; the barbs are located on the (Continued)

curved surface of the microneedle and are inclined toward the polymeric procoagulant base. The fabrication method includes using a mold pore-forming, a porogen pore-forming, or a thermally induced phase separation pore-forming, and combining the barbed microneedle while forming the microporous structure to obtain a suture-free coagulation-assisted fixed cardiac patch.

6 Claims, 3 Drawing Sheets

(56) References Cited

FOREIGN PATENT DOCUMENTS

| | | |
|---|---|---|
| CN | 112972433 A | 6/2021 |
| CN | 113069241 A | 7/2021 |
| CN | 113244016 A | 8/2021 |
| CN | 113425897 A | 9/2021 |
| CN | 113907915 A | 1/2022 |

OTHER PUBLICATIONS

Junnan Tang, et al., Cardiac cell-integrated microneedle patch for treating myocardial infarction, Science Advances, 2018, pp. 1-12, vol. 4 No. 11, aat9365.
Brian W. Walker, et al., Engineering a naturally-derived adhesive and conductive cardiopatch, Biomaterials., 2019, pp. 1-28, vol. 207.
Miles Montgomery, et al., Flexible shape-memory scaffold for minimally invasive delivery of functional tissues, Nature Materials, 2017, pp. 1-9.

SUTURE-FREE COAGULATION-ASSISTED FIXED CARDIAC PATCH AND PREPARATION METHOD THEREOF

CROSS REFERENCE TO THE RELATED APPLICATIONS

This application is the national phase entry of International Application No. PCT/CN2022/109644, filed on Aug. 2, 2022, which is based upon and claims priority to Chinese Patent Application No. 202111133190.0, filed on Sep. 27, 2021, the entire contents of which are incorporated herein by reference.

TECHNICAL FIELD

The present invention belongs to the technical field of biomedical materials, and more particularly, relates to a suture-free coagulation-assisted fixed cardiac patch and fabrication method thereof.

BACKGROUND

Myocardial infarction is a common and highly fatal cardiovascular disease, the main cause is myocardial necrosis caused by myocardial hypoxia and ischemia. Compared with traditional methods such as drugs and cell therapy, cardiac patches inhibit left ventricular remodeling, slow down heart failure, and maintain cardiac function by providing mechanical support to the infarcted myocardium, which is a promising treatment method and can be combined with stem cell and drug therapy.

The current implantation methods for cardiac patches are mostly sutures and adhesives, and the suturing method has problems such as complicated surgical procedure, large trauma, susceptibility to postoperative complications, and long recovery time (seen in Reference 1 *An Elastic, Biodegradable Cardiac Patch Induces Contractile Smooth Muscle and Improves Cardiac Remodeling and Function in Subacute Myocardial Infarction [J]. Journal of the American College of Cardiology*, 2007, 49 (23): 2292-2300), while the adhesive method has problems that the patch does not fit firmly and tends to slip off (seen in Reference 2 *Engineering a naturally-derived adhesive and conductive cardiopatch [J]. Biomaterials*, 2019, 207 and Reference 3 *Flexible shape-memory scaffold for minimally invasive delivery of functional tissues [J]. Nature Materials*, 2017). Adding a microneedle array to the side of the patch facing the heart has been proven to assist in patch fixation, the microneedles are mostly conical in shape and have no barb structure, and the patch bases are mostly smooth structures (seen in Reference 4 *Cardiac cell-integrated microneedle patch for treating myocardial infarction [J]. Science Advances*, 2018, 4 (11)). This kind of cardiac patch base still leaves a gap between the patch and the myocardium when working and cannot fit completely.

Therefore, it is of great significance to develop a suture-free cardiac patch with good fixation.

SUMMARY

In order to solve the problems in the prior art, the invention provides a suture-free coagulation-assisted fixed cardiac patch and fabrication method thereof. The invention introduces barbed microneedles on one side of the polymeric procoagulant base, and designs a microporous structure on the same side to form a cardiac patch, and this cardiac patch with barbed structure and microporous structure is sent to the site of myocardial infarction by thoracoscopic surgery, achieving suture-free fixation of the patch through the self-locking effect of the barbed structure and the coagulation and adhesion functions of the microporous structure. Compared with the traditional cardiac patch, the cardiac patch of the invention uses barbed microneedles to achieve suture-free fixation in the animal body, and uses the microporous structure of the patch base to promote coagulation reaction to fix the myocardium and the patch, and avoids the suturing process during the cardiac patch implantation by co-fixing and combining the myocardium and the patch, and the base is a solid structure except for the microporous structure on the surface, which provides a stronger mechanical effect than a non-solid structure.

To this end, the technical schemes of the invention are as follows:

A suture-free coagulation-assisted fixed cardiac patch, comprising that a polymer procoagulant base and several barbed microneedles fixed on the polymer procoagulant base, and a side surface of the polymer procoagulant base with the microneedle has a microporous structure which does not penetrate a solid base of the polymer;

wherein the barbed microneedle is a microneedle with barbs, an included angle α between the microneedle and a plane where the polymer procoagulant base located is 60-90°, and the microneedles are evenly distributed on the polymeric procoagulant base (avoiding stress concentration) with a density of 5-50 threads/cm$^2$; wherein the barbs are located on the curved surface of the microneedle (the rotating surface of the microneedle column) and inclined toward the polymeric procoagulant base;

wherein a material of the polymer procoagulant base is more than one selected from polyurethane, silicone rubber, polyurethane-polyurea, and polylactic acid-polycaprolactone, which is a biodegradable, biocompatible and deformable base.

The barbs of the barbed microneedle are located on the peripheral surface of the microneedle, and all barbs are oriented toward the polymeric procoagulant base to ensure that the barbs can penetrate the tissue smoothly, and are difficult to pull out of the tissue after penetration to form self-locking.

The microporous structure is located only on the side of the base facing the myocardium, the side in contact with the myocardium, and does not penetrate the entire base. The rest of the base is made of solid polymer material, which provides sufficient mechanical properties for the cardiac patch, while the microporous structure increases the specific surface area of the polymeric procoagulant base, which plays a role in promoting blood coagulation when myocardial hemorrhage caused by the microneedle insertion into the myocardium.

The suture-free coagulation-assisted fixed cardiac patch of the invention can be sent to the site of myocardial infarction by thoracoscopic surgery, the barbed microneedle is inserted into the infarction site to fix the cardiac patch by the function of the barbed structure and the coagulation function of the microporous structure, to achieve the suture-free effect of the cardiac patch.

In the present invention, the self-locking fixation effect of the barbed microneedles on the surface of the cardiac patch and the synergistic fixation effect of the coagulation-based adhesion between the patch and the myocardium are the keys to supporting the suture-free fixation of the cardiac patch. The barbed microneedles attached to the patch in an array form can achieve self-locking fixation immediately when the microneedle array is inserted into the myocardium; the small amount of blood flowing out when the microneedle is inserted into the myocardium can be coagulated, and the patch between the microneedles and with microporous structure on the surface adheres to the myocardium. The synergy between the two fixations of barbed microneedles and microporous coagulation is reflected in:

(1) barbed microneedles and microporous coagulation each provide a fixation effect, and the superimposed fixation effect of the two is more effective than a single fixation mechanism;

(2) for cardiac patches that only contains barbed microneedles without a microporous structure, the fixation force of the barbed microneedles is concentrated on the microneedles arranged in the array, and the stress is concentrated on the microneedles, resulting in unequal stresses on the tissue (cardiac patch), which will lead to: firstly, the junction between the microneedle and the patch material is more likely to be damaged due to stress concentration; secondly, the tissue between the microneedles is insufficient in mechanical support, thereby reducing the therapeutic effect; thirdly, the stretching and contracting actions of the heart will also cause undesirable deformations (i.e. warping and bending) of the cardiac patch, further reduces the therapeutic effect of the cardiac patch;

the invention combines microneedles and microporous structures, and coagulates and adheres through micropores. On the one hand, the stress on the myocardial tissue and the patch itself is more uniform, and the therapeutic effect is enhanced, reflected in that both the damage of the cardiac patch and undesired deformation of the cardiac patch are avoided. This is because: the cardiac patch used in the invention is a base with a certain elastic material, which provides the cardiac patch with the ability to deform, and the self-locking fixation effect of the microneedles with barbs attached to the patch in the array makes the cardiac patch synchronise with and even consistent with the deformation caused by the stretching and contracting movements of the heart, thereby avoiding warping and bending of the cardiac patch during work.

(3) using coagulation and adhesion alone, due to the long coagulation time, the patch cannot be fixed on the heart surface at the first time of implantation, which reduces the adhesion effect in the light case and fails to fix it in the heavy case, especially when carrying out subsequent minimally invasive implantation experiments; the adhesion of microporous coagulation itself is also low, which may loosen or fail during long-term use; it is also difficult to create tiny bleeding points in the minimally invasive surgery on the surface of the patient's heart in the required part. The use of barbed microneedles can compensate for these shortcomings. Therefore, the joint use of barbed microneedles and microporous coagulation can solve and improve related problems.

The following preferred technology program is presented to give a detailed description for this invention:

The said suture-free coagulation-assisted fixed cardiac patch, wherein a cross-sectional shape of the barbs is more than one selected from round, triangular, square, wedge, oval, octagonal, rectangular or flat;

wherein 3-6 groups of barbs are distributed along the longitudinal direction of the microneedle, each group consisting of 2-4 barbs, and from the cross-section of the barbed microneedle, each barb in each group of barbs is equidistantly located on the circumference of the cross-section;

wherein an included angle between the barb and the microneedle is greater than 0° and less than or equal to 90° (preferably) 30°;

wherein one end of the microneedle is a beveled needle tip (obtained by mechanical or laser cutting or by casting or 3D printing, one end is a bevel tip shape to easily penetrate into cardiac tissue), the other end is a flat surface, and the end of the flat surface is fixedly bonded to the polymer procoagulant base; wherein an included angle between a bevel of the beveled needle tip and an axial direction of the microneedle is 5-45° (preferably) 30°. The head end of the microneedle used in the invention is a beveled needle tip, and the included angle between the bevel of the beveled needle tip and the axial direction of the microneedle, the length of the microneedle and the stiffness of the microneedle will affect the difficulty of penetration, the smaller the included angle between the bevel of the beveled needle tip and the axial direction of the microneedle, the easier it is to penetrate.

A suture-free coagulation-assisted fixed cardiac patch, wherein a length of the microneedle is 1-5 mm (preferably 2-3 mm); wherein a material of the barbed microneedle is more than one selected from polylactic acid, polycaprolactone, PDO, polyethylene and polypropylene (preferably polycaprolactone or polypropylene). The beveled needle tip at the head end of the microneedle has strong pressure, and the microneedle is only 5 mm in length, which is not easy to bend (the moment is small), and the selection of rigid biomaterials can ensure that the barbed microneedle can be inserted into the cardiac tissue. The shorter the length of the microneedle, the easier it is to penetrate, but if it is too short, it will affect the fixation, and the stiffness of the microneedle is affected by the raw material, the greater the stiffness, the easier it is to penetrate. The larger the density of the microneedle, the better the fixation effect, but if it is too dense, it will produce resistance to the beating of the heart, and if the density of the barb is too small, it will not be suture-free, if the density of the barb is too large, it will cause great damage to the tissue and the suture-free effect will also be worse; there is a relationship between the length of the microneedle and the density of the barb, the length of the microneedle and the density of the barb determine the number of barbs on a microneedle, and it is possible to adjust the length and the density of the barb in order to achieve the best fixation effect.

The said suture-free coagulation-assisted fixed cardiac patch, calculated by taking a scanning electron microscope (SEM) and the accompanying scale, an average pore diameter of the microporous structure is 50-200 µm, an average depth of the micropores is 20-120 mm, and an density of the micropores is 25-400/mm$^2$ (the density refers to the number per unit area). When the average pore diameter, average depth, and density of the micropores are too low, the blood flowing into the micropores will be less, and the accumulation of fibrin and platelets will also be less, resulting in a lower coagulation effect; if the pore diameter is too large, the specific surface area will be insufficient, and will not be enough to produce a sufficient coagulation binding effect; if the depth of the micropores is too deep, the blood will not be able to enter efficiently, so the depth of the micropores should not be too large.

The invention also provides the method of fabricating the suture-free coagulation-assisted fixed cardiac patch, comprising the following steps:
  (1) printing a model A by 3D printing, wherein the model A comprises the base, with several columns and spherical concave structures formed on a side surface of the base, and several columns are perpendicular to the side surface; the number of several columns is the same as the number of several barbed microneedles;
  (2) fixing the model A horizontally in a container with the columns facing upwards, and pouring a polydimethylsiloxane (PDMS) solution into the container to completely cover the model A, removing bubbles, then heating and curing to obtain a mold B;
  wherein the mold B has a column hole structure and a spherical protrusion structure, the column hole structure being formed by columns on the model A, and the spherical protrusion structure being formed by the spherical concave structure on the model A;
  (3) first, inserting the barbed microneedle dipped in high-temperature paraffin into the column hole of the mold B (the high-temperature paraffin plays a role of wrapping and isolation), a barb direction (the direction of the barb in the invention refers to the general direction of the tip of the barb) is opposite to an insertion direction, and the barbed microneedle corresponds to the column hole one by one; then casting a solution a on the mold B arranged with a microneedle array and locating on the side pointed by the barb direction; finally, after a solvent in the solution A is completely volatilized, removing the mold B, paraffin and excess barbed microneedles; wherein a solid structure is formed during the volatilization;
  wherein the solution a is obtained by dissolving the polymer used to form the polymeric procoagulant base in a hexafluoroisopropanol solution or a dioxane solution.

The micropores obtained by the method of mold pore-forming are consistent in size and shape, regularly arranged, and have adjustable porosity.

The invention also provides the method of fabricating the suture-free coagulation-assisted fixed cardiac patch, comprising the following steps:
  (1) printing a model C by 3D printing, the model C comprises the base, with several columns formed on the side surface of the base, and several columns are perpendicular to the side surface; the number of several columns is the same as the number of several barbed microneedles;
  (2) fixing the model C horizontally in the container with the columns facing upwards, and pouring the polydimethylsiloxane (PDMS) solution into the container to completely cover the model C, removing bubbles, then heating and curing to obtain a mold D;
  wherein the mold D has the column hole structure, and the column hole structure is formed by columns on the model C;
  (3) first, inserting the barbed microneedle into the column hole of the mold D, the barb direction being the same as the insertion direction, and the barbed microneedle corresponding to the column hole one by one; then casting a solution b several times on the mold D arranged with the microneedle array and located on the side opposite to the barb direction, and after the last casting, evenly distributing a porogen in the solution b which does not completely volatilize the solvent, finally, after the solvent is completely volatilized, removing the mold D, the porogen and excess barbed microneedles; wherein the solid structure is formed during the volatilization;
  wherein the porogen is NaCl particles or gelatin microspheres;
  wherein the solution b is obtained by dissolving the polymer used to form the polymeric procoagulant base in the hexafluoroisopropanol solution or the dioxane solution.

The pore diameter of the micropores obtained by the method of porogen pore-forming is adjustable and varies with the size of the porogen, and the micropores have a low degree of regularity.

The invention also provides the method of fabricating the suture-free coagulation-assisted fixed cardiac patch, comprising the following steps:
  (1) printing a model E by 3D printing, wherein the model E comprises the base, with several columns formed on the side surface of the base, and several columns are perpendicular to the side surface; the number of several columns is the same as the number of several barbed microneedles;
  (2) fixing the model E horizontally in the container with the columns facing upwards, and pouring the polydimethylsiloxane (PDMS) solution into the container to completely cover the model E, removing bubbles, then heating and curing to obtain a mold F;
  wherein the mold F has the column hole structure, and the column hole structure is formed by columns on the model E;
  (3) first, inserting the barbed microneedle into the column hole of the mold F, the barbed direction being the same as the insertion direction, and the barbed microneedle corresponding to the column hole one by one;
  (4) along the insertion direction, casting a solution c over the column holes of the mold F arranged with the microneedle array, and forming the solid structure after the solvent in the solution c is completely volatilized; wherein the solution c is obtained by dissolving the polymer used to form the polymeric procoagulant base in the hexafluoroisopropanol solution or the dioxane solution;
  (5) along the insertion direction, casting a solution d over the polymer in the mold F obtained in step (4), and using a thermally induced phase separation method to completely remove the solvent in the solution d to obtain the microporous structure, finally removing the mold F and excess barbed microneedles; wherein the solution d is obtained by dissolving the polymer in the dioxane solution.

The micropores obtained by the method of thermally induced phase separation pore-forming have a uniform distribution of pore diameter, high porosity and good strength, but are easy to produce a compact skin layer and a closed hole.

The patch base of the invention is a polymer film formed by a solute after the solvent evaporates, and while the polymer film is formed, the barbed microneedles are fixed according to the arranged array, there is no need to carry out a secondary process to complete the connection and fixation of the microneedles and the base.

The barbed microneedle is prepared by cutting the barbed suture to the required length, one end of the microneedle is the beveled needle tip (obtained by mechanical or laser cutting), the other end is a flat surface.

Alternatively, the barbed microneedle is produced by casting or 3D printing.

The invention also provides the method of fabricating the suture-free coagulation-assisted fixed cardiac patch, comprising the following steps:
(1) printing a model G by 3D printing, wherein the model G comprises the base, with several columns formed on the side surface of the base, and several columns are perpendicular to the side surface; the number of several columns is the same as the number of several barbed microneedles;
(2) fixing the model G horizontally in a container x with the columns facing upwards, and pouring the polydimethylsiloxane solution into the container to completely cover the model G, removing bubbles, then heating and curing to obtain a mold H;
wherein the mold H has the column hole structure, and the column hole structure is formed by columns on the model G; wherein an inner diameter of the column hole is 80-110% of a diameter of the microneedle; since the material of the mold H in the invention is silicone rubber, which has good elasticity, and the surface of the column hole obtained by the said method is smooth, which ensures that when the barbed microneedle is inserted, it will be squeezed and temporarily fixed.
(3) first, inserting the barbed microneedle into the column hole of the mold H, the barb direction being opposite to the insertion direction, the barbed microneedle corresponding to the column hole one by one, and one end of the barbed microneedle being exposed outside the column hole; mixing a mixture of a prepolymer of dimethylsiloxane and an initiator, then pouring it into a container y; and then evenly distributing NaCl particles or gelatin microspheres on the surface of the mixture, inverting the mold H to insert the barbed microneedle exposed outside the column hole into the mixture, finally, removing the mold H and the porogen after the solution is cured by heat to form a silicone rubber.

The method of fabricating the suture-free coagulation-assisted fixed cardiac patch is mainly based on the complex structure of the cardiac patch in the invention, compared to the cardiac patch with barbed microneedles only, the microporous structure and its ideal distribution is difficult to achieve; therefore, the invention introduces the barbed microneedle during the formation of the polymeric procoagulant base, and also introduces the simultaneous formation of the microporous structure in the process, the method of combining the barbed microneedles and forming the microporous structure at one time is simple and easy to implement; moreover, the introduction of the barbed microneedle during the formation of the polymeric procoagulant base also optimizes the bonding strength between the microneedle and the polymeric procoagulant base because: there are barbs on the surface of the barbed microneedle, and the polymeric procoagulant base is formed by casting from a solution; introducing the barbed microneedle before the polymeric procoagulant base is formed, to maximizes the contact area between the microneedle and the polymeric procoagulant base, resulting in a strong bond, which ensures the synergistic fixation effect of the self-locking fixation effect of the barbed microneedle on the surface of the cardiac patch and the coagulation-based adhesion between the patch and the cardiac muscle.

Benefits:
(1) The said suture-free coagulation-assisted fixed cardiac patch of the invention, has barbed structured microneedles in the z-axis direction of the polymer procoagulant base, and designs a microporous structure on the same side, so that when implanted in an infarcted myocardial site, it can be carried out through a thoracoscopic surgery without suture fixation, etc., reducing the difficulty of the operation and postoperative complications.
(2) The said suture-free coagulation-assisted fixed cardiac patch of the invention, the insertion of the microneedle causes myocardial hemorrhage and exposes vascular endothelial tissue after vascular injury, at this time, under the interaction of platelet activation and systemic activation of coagulation, the formation of the platelet hemostatic thrombus and the fibrin ultimately leads to the formation of blood clots; due to the presence of microporous structure, the patch base has a larger specific surface area, which allows for the accumulation of more platelets and fibrin, thereby accelerating the formation of blood clots, then accelerating the fixation between the myocardium and the patch.
(3) The said suture-free coagulation-assisted fixed cardiac patch of the invention, the solid structure on the patch has good mechanical properties (the Young's modulus of the patch without microporous structure is about 340 kPa, while the Young's modulus of the patch with a microporous structure on the surface only is about 250-270 kPa, and the Young's modulus of the patch with a microporous structure penetrating through is about 200 kPa), and it has a better cardiac repairing effect by co-fixing with the microneedle and combining myocardium and the patch.
(4) The said suture-free coagulation-assisted fixed cardiac patch of the invention, while the polymer film is formed, the barbed microneedles are fixed according to the arranged array, there is no need to perform a secondary process to complete the connection and fixation of the microneedles and the base.

DETAILED DESCRIPTION OF THE EMBODIMENTS

Figure 1A:
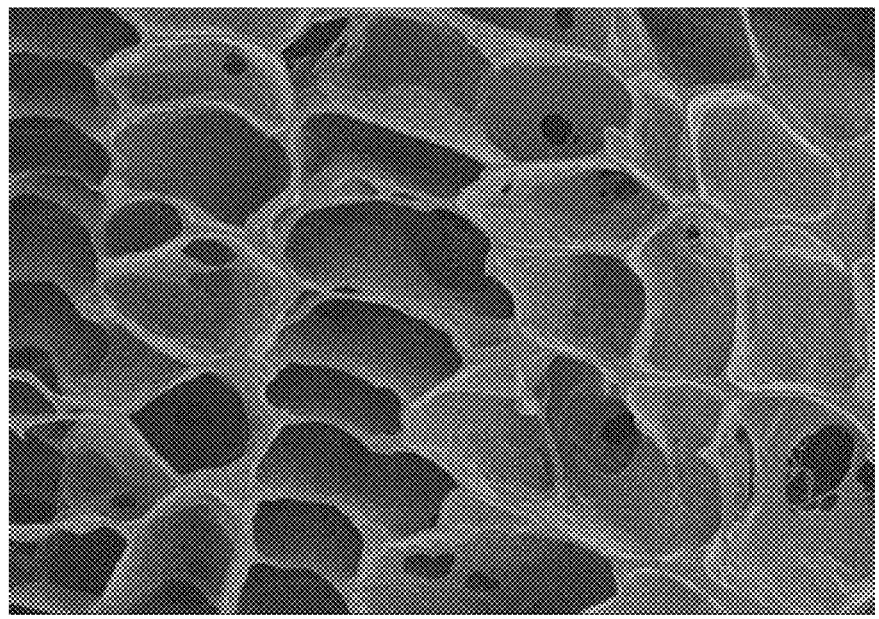
FIG. 1A is an SEM diagram of the microporous structure on the polymeric procoagulant base.

Based on above mentioned method, the following embodiments are carried out for further demonstration of the present invention. It is to be understood that these embodiments are only intended to illustrate the invention and are not intended to limit the scope of the invention. In addition, it should be understood that after reading the contents described in the present invention, those technical personnel in this field can make various changes or modifications to the invention, and these equivalent forms also fall within the scope of the claims attached to the application.

The structure of the barbed microneedle in the invention is as follows:

the barbed microneedle is a microneedle with barbs, one end of the microneedle (diameter 0.3-0.5 mm) is a beveled needle tip, and the barb faces away from the tip; the cross-sectional shape of the barb is more than one selected from round, triangular, square, wedge, oval, octagonal, rectangular or flat; the barb is located on the curved surface of the microneedle. The included angle between the bevel of the beveled needle tip and the axial direction of the microneedle is 5-45°.

3-6 groups of barbs are distributed along the longitudinal direction of the microneedle, each group consisting of 2-4 barbs, and from the cross-section of the barbed microneedle, each barb in each group of barbs is equidistantly located on the circumference of the cross-section;

wherein an included angle between the barb and the microneedle is greater than 0° and less than or equal to 90°.

The material of the barbed microneedle is more than one selected from polylactic acid, polycaprolactone, PDO, polyethylene and polypropylene.

Since the basic function of the barbed microneedle is to fix the base, the structure of the barbed microneedle in the invention ensures a good fixing effect and can cooperate with the polymeric procoagulant base to achieve the optimal therapeutic effect.

When the barbed microneedle is designed, the performance of the barbed microneedle is evaluated by using a universal mechanical testing machine (Instron 5543A), specifically, the force when the microneedle is pulled out of the chicken breast after being inserted into the chicken breast is measured, and the operation process is as follows:

turn on the switch of the universal mechanical testing machine, cut the chicken breast by using a scalpel into rectangular blocks with a thickness of about 5 mm, a length of 3-4 cm, and a width of 1-2 cm, and place them on the smooth base of the testing machine; replace the instrument for compressing on the upper part of the testing machine with a stretching clamp, use tweezers to clamp the barbed microneedle to about 5-10 mm from the needle tip, and insert the needle tip vertically into the chicken breast surface until the 3.5 mm mark is just inserted into the chicken breast; clamp the upperend label of the suture by the clamp, and move the position of the chicken breast to make the suture in a vertical state. Open the Bluehill software, fix the chicken chest by tweezers and set the experiment to stop after a displacement of 5 mm. Start the tensile experiment to measure the maximum force required to pull out the suture completely. Remove the suture, change the position of the suture tied into the chicken breast, and repeat the above operation 4 times. If the tip of the suture becomes worn and bent during the experiment, the worn and bent part of the tip needs to be cut off to keep the tip sharp and re-marked, then continue the experiment. Record the experimental data.

After calculating the average value, the force of the barbed microneedle required to be pulled out from the tissue ranges from 0.1-0.35 N, while the force of the smooth microneedle (i.e, the microneedle without barbs) required to be pulled out of the tissue is much less than 0.1 N, or even negligible.

Example 1

A method of fabricating the suture-free coagulation-assisted fixed cardiac patch, comprising the following steps:

The Preparation of Raw Materials:

Barbed microneedle: the diameter of the microneedle is 0.4 mm, and the included angle between the bevel of the beveled needle tip and the axial direction of the microneedle is 30°; the cross-sectional shape of the barb is triangular; 3 groups of barbs are distributed along the longitudinal direction of the microneedle, each group consists of 3 barbs, and the included angle between the barb and the microneedle is 30°; the material of the barbed microneedle is polylactic acid.

The universal mechanical testing machine (Instron 5543A) is used to measure the force when the barbed microneedle is pulled out of the chicken breast after being inserted into the chicken breast, which is 0.122 N.

Figure 1B:
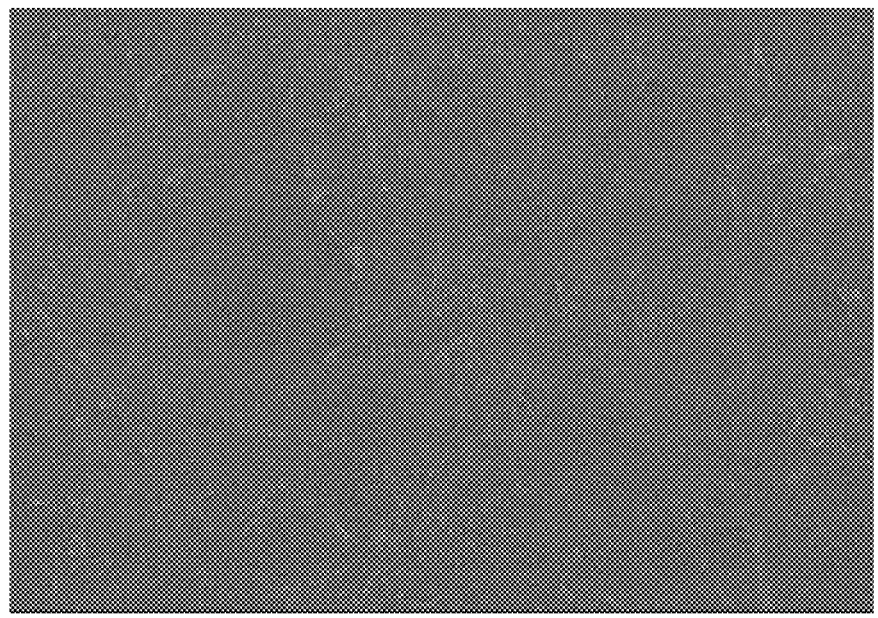
FIG. 1B is an SEM diagram of a cross-section of a solid part on the polymeric procoagulant base.
Figure 2:
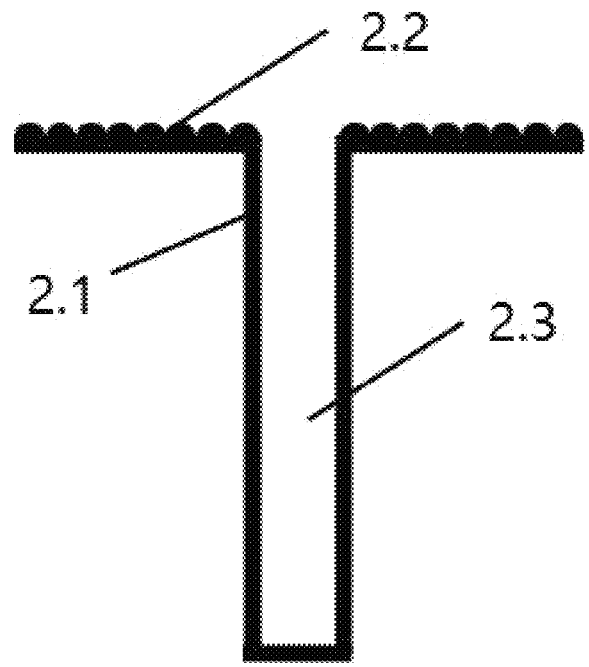
FIG. 2 is a partial schematic diagram of the mold B; wherein the numbers in the figure refer to: 2.1—mold B, 2.2—spherical protrusion structure, 2.3—column hole structure on the mold B.

(1) Printing the model A by 3D printing, the model A consists of the base, with several columns and spherical concave structures are formed on the side surface of the base, and several columns are perpendicular to the side surface;

(2) fixing the model A horizontally in a container with the columns facing upwards, and pouring the polydimethylsiloxane solution into the container to completely cover the model A, removing bubbles, then heating and curing to obtain a circular mold B with a diameter of 8 mm;

wherein the mold B 2.1 has column hole structures 2.3 (evenly distributed on the edge of the circular mold and the number is 4) and a spherical protrusion structure 2.2 (evenly distributed on the upper surface of the mold), the column hole structure being formed by columns on the model A, and the spherical protrusion structure being formed by the spherical concave structure on the model A; the partial schematic diagram is shown in FIG. 2;

(3) first inserting the barbed microneedle (4 pieces, and the length of the microneedle is 3 mm) dipped in high-temperature paraffin into the column hole of the mold B, the barbed direction is opposite to the insertion direction, and the barbed microneedle corresponds to the column hole one by one; then casting the solution a (obtained by dissolving polyurethane in the hexafluoroisopropanol solution, and the concentration is 0.1 g/mL) on the mold B arranged with the microneedle array and located on the side pointed by the barb direction; finally after the solvent in the solution a is completely volatilized, removing the mold B, paraffin and excess barbed microneedles, forming the solid structure during the volatilization and obtaining the suture-free coagulation-assisted fixed cardiac patch;

The prepared suture-free coagulation-assisted fixed cardiac patch, comprises the polymer procoagulant base and the barbed microneedle fixed on the polymer procoagulant base (the material is polyurethane and the thickness is 0.4 mm), and the side surface of the polymer procoagulant base with the microneedle has a microporous structure that does not penetrate the solid base of the polymer (as shown in FIGS. 1A-1B); the average pore diameter of the microporous structure is 100 μm, the average depth of the micropores is 80 mm, and the density of the micropores is 100/mm². The included angle α between the microneedle of the barbed microneedle and the plane where the polymer procoagulant base located is 90°; the barbs are inclined toward the polymeric procoagulant base; the end of the flat surface of the microneedle is fixedly connected to the polymer procoagulant base.

Example 2

Figure 3:
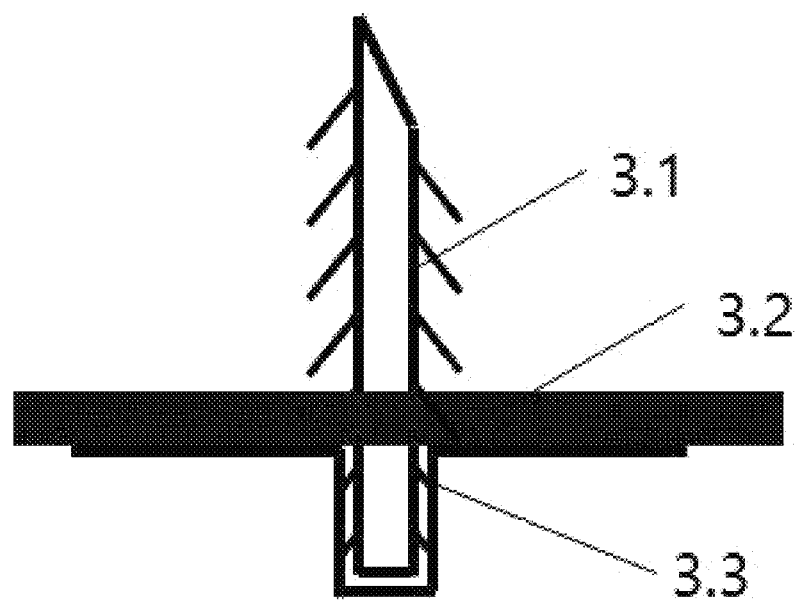
FIG. 3 is a schematic diagram of the positional relationship of the barbed microneedle inserted into the column hole of the mold D; wherein the numbers in the figure refer to: 3.1—barbed microneedle in the mold D, 3.2—mold D, 3.3—column hole on mold D.

A method of fabricating the suture-free coagulation-assisted fixed cardiac patch, comprising the following steps:
The Preparation of Raw Materials:
Barbed microneedle: the diameter of the microneedle is 0.5 mm, and the included angle between the bevel of the beveled needle tip and the axial direction of the microneedle is 30°; the cross-sectional shape of the barb is triangular; 4 groups of barbs are distributed along the longitudinal direction of the microneedle, each group consists of 3 barbs, and the included angle between the barb and the microneedle is 30°; the material of the barbed microneedle is polycaprolactone.
The universal mechanical testing machine (Instron 5543A) is used to measure the force when the barbed microneedle is pulled out of the chicken breast after being inserted into the chicken breast, which is 0.200 N.
Porogen: use a sieve to screen out gelatin microspheres with a diameter of 100 μm.
(1) Printing a model C by 3D printing, the model C comprises the base, with several columns formed on the side surface of the base, and several columns are perpendicular to the side surface; the number of several columns is the same as the number of several barbed microneedles;
(2) fixing the model C horizontally in the container with the columns facing upwards, and pouring the polydimethylsiloxane solution into the container to completely cover the model C, removing bubbles, then heating and curing to obtain a circular mold D with a diameter of 8 mm;
wherein the mold D has the column hole structure (evenly distributed at the edge of the circular mold and the number is 4), and the column hole structure is formed by columns on the model C;
(3) first inserting the barbed microneedle 3.1 (4 pieces, and the length of the microneedle is 4 mm) into the column hole 3.3 of the mold D 3.2, the barbed direction is the same as the insertion direction, and the barbed microneedle corresponds to the column hole one by one, the schematic diagram of the position is shown in FIG. 3; then casting the solution b (obtained by dissolving polyurethane in the hexafluoroisopropanol solution, and the concentration is 0.1 g/mL) 4 times (0.25 mL each) on the mold D arranged with the microneedle array and located on the side opposite to the barb direction, and after the last casting, evenly distributing a porogen in the solution b which does not completely volatilize the solvent, finally after the solvent is completely volatilized, removing the mold D, the porogen and excess barbed microneedles, forming the solid structure during the volatilization and obtaining the suture-free coagulation-assisted fixed cardiac patch;
The prepared suture-free coagulation-assisted fixed cardiac patch, comprises the polymeric procoagulant base and the barbed microneedle fixed on the polymer procoagulant base (the material is polyurethane and the thickness is 0.4 mm), and the side surface of the polymeric procoagulant base with the microneedle has a microporous structure that does not penetrate the solid base of the polymer; the average pore diameter of the microporous structure is 100 μm, the average depth of the micropores is 80 mm, and the density of the micropores is 100/mm². The included angle α between the microneedle of the barbed microneedle and the plane where the polymer procoagulant base located is 90°; the barbs are inclined toward the polymeric procoagulant base; the end of the flat surface of the microneedle is fixedly connected to the polymer procoagulant base.

Example 3

A method of fabricating the suture-free coagulation-assisted fixed cardiac patch, comprising the following steps:
The Preparation of Raw Materials:
Barbed microneedle: the diameter of the microneedle is 0.4 mm, and the included angle between the bevel of the beveled needle tip and the axial direction of the microneedle is 30°; the cross-sectional shape of the barb is square; 5 groups of barbs are distributed along the longitudinal direction of the microneedle, each group consists of 3 barbs, and the included angle between the barb and the microneedle is 30°; the material of the barbed microneedle is polypropylene.
The universal mechanical testing machine (Instron 5543A) is used to measure the force when the barbed microneedle is pulled out of the chicken breast after being inserted into the chicken breast, which is 0.220 N.
(1) Printing a model E by 3D printing, the model E consists of the base, with several columns formed on the side surface of the base, and several columns are perpendicular to the side surface; the number of several columns is the same as the number of several barbed microneedles;
(2) fixing the model E horizontally in the container with the columns facing upwards, and pouring the polydimethylsiloxane solution into the container to completely cover the model E, removing bubbles, then heating and curing to obtain a circular mold F with a diameter of 8 mm;
wherein the mold F has the column hole structure (evenly distributed at the edge of the circular mold and the number is 4), and the column hole structure is formed by columns on the model E;
(3) first inserting the barbed microneedle (4 pieces, and the length of the microneedle is 4 mm) into the column hole of the mold F, the barbed direction is the same as the insertion direction, and the barbed microneedle corresponds to the column hole one by one;
(4) along the insertion direction, casting (3 times in total, 0.25 mL each) the solution c (obtained by dissolving polyurethane in the hexafluoroisopropanol solution, and the concentration is 0.1 g/mL) over the column holes of the mold F arranged with the microneedle array, and forming the solid structure after the solvent in the solution c is completely volatilized;
(5) along the insertion direction, casting (0.25 mL) the solution d (using a dioxane solution as a solvent to prepare a 6% w/v polyurethane solution) over the polymer in the mold F obtained in step (4), and using a thermally induced phase separation method to completely remove the solvent in the solution d to obtain the microporous structure, finally removing the mold F and excess barbed microneedles, and obtaining the suture-free coagulation-assisted fixed cardiac patch; wherein the specific process of completely removing the solvent from the solution d to obtain the microporous structure by using the thermally induced phase separation method is as follows: preheating at 37° C.

for 1 hour, then transferring to −20° C. and leaving overnight to completely crystallize the dioxane; then freeze-drying the cured solution d under vacuum at −20° C.

The prepared suture-free coagulation-assisted fixed cardiac patch, comprises the polymer procoagulant base and the barbed microneedle fixed on the polymer procoagulant base (the material is polyurethane and the thickness is 0.4 mm), and the side surface of the polymer procoagulant base with the microneedle has a microporous structure that does not penetrate the solid base of the polymer; the average pore diameter of the microporous structure is 100 μm, the average depth of the micropores is 80 mm, and the density of the micropores is 100/mm$^2$. The included angle α between the microneedle of the barbed microneedle and the plane where the polymer procoagulant base located is 90°; the barbs are inclined toward the polymeric procoagulant base; the end of the flat surface of the microneedle is fixedly connected to the polymer procoagulant base.

Example 4

A method of fabricating the suture-free coagulation-assisted fixed cardiac patch, comprising the following steps:
The Preparation of Raw Materials:

Barbed microneedle: the diameter of the microneedle is 0.4 mm, and the included angle between the bevel of the beveled needle tip and the axial direction of the microneedle is 30°; the cross-sectional shape of the barb is triangular; 4 groups of barbs are distributed along the longitudinal direction of the microneedle, each group consists of 4 barbs, and the included angle between the barb and the microneedle is 30°; the material of the barbed microneedle is polylactic acid.

The universal mechanical testing machine (Instron 5543A) is used to measure the force when the barbed microneedle is pulled out of the chicken breast after being inserted into the chicken breast, which is 0.210 N.

Porogen: use a sieve to screen out NaCl particles with a diameter of 100 μm.

Figure 4:
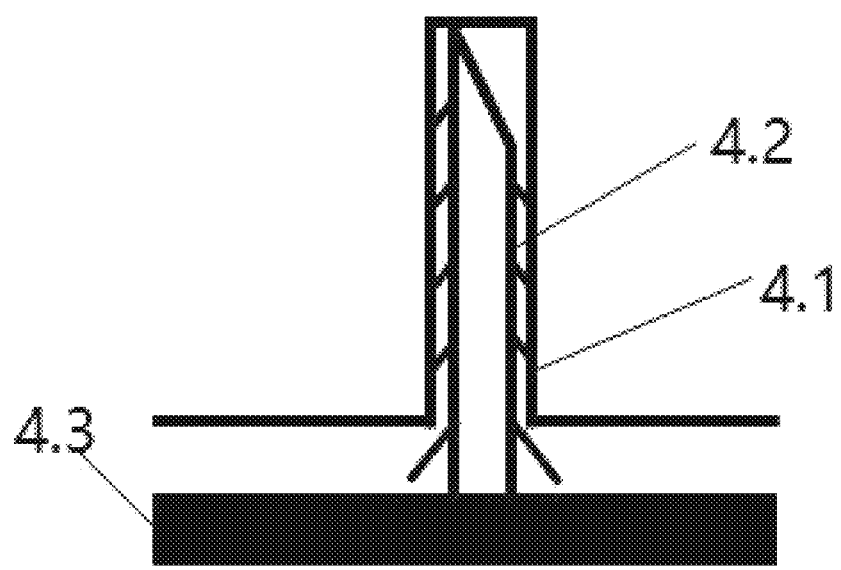
FIG. 4 is a schematic diagram of the positional relationship of the barbed microneedles located in the mold H inserted into the mixture, wherein the numbers in the figure refer to: 4.1—mold H, 4.2—barbed microneedles in the mold H, 4.3—mixture.

(1) printing a model G by 3D printing, wherein the model G comprises the base, with several columns formed on the side surface of the base, and several columns are perpendicular to the side surface; the number of several columns is the same as the number of several barbed microneedles;
(2) fixing the model G horizontally in a container x with the columns facing upwards, and pouring the polydimethylsiloxane solution into the container to completely cover the model G, removing bubbles, then heating and curing to obtain a circular mold H with a diameter of 8 mm;
wherein the mold H has the column hole structure (evenly distributed on the edge of the circular mold and the number is 4), and the column hole structure is formed by columns on the model G; wherein an inner diameter of the column hole is 90% of a diameter of the microneedle;
(3) first inserting the barbed microneedle (4 pieces, and the length of the microneedle is 4 mm) into the column hole of the mold H, the barb direction is opposite to the insertion direction, the barbed microneedle corresponds to the column hole one by one, and one end of the barbed microneedle is exposed outside the column hole; mixing a mixture of the prepolymer of dimethylsiloxane and the initiator (the mass ratio of the prepolymer and the initiator is 10:1, stirring evenly and removing bubbles), then pouring into a container y; and then evenly distributing the porogen on the surface of the mixture, inverting the mold H 4.1 to make the barbed microneedle 4.2 exposed outside the column hole into the mixture 4.3, the schematic diagram of the position is shown in FIG. 4 (after the mixture is poured into container y, the amount is less than the volume of container y and immerse 1-2 mm of the lower portion of the microneedle), finally removing the mold H and the porogen after the solution is cured by heat to form a silicone rubber, and obtaining the suture-free coagulation-assisted fixed cardiac patch.

The prepared suture-free coagulation-assisted fixed cardiac patch, comprises the polymer procoagulant base and the barbed microneedle fixed on the polymer procoagulant base (the material is silicone rubber), and the side surface of the polymer procoagulant base with the microneedle has a microporous structure that does not penetrate the solid base of the polymer; the average pore diameter of the microporous structure is 100 μm, the average depth of the micropores is 80 mm, and the density of the micropores is 100/mm$^2$. The included angle α between the microneedle of the barbed microneedle and the plane where the polymer procoagulant base located is 90°; the end of the flat surface of the microneedle is fixedly connected to the polymer procoagulant base.

The fixation and treatment effects of the cardiac patch and myocardial tissue in Examples 1-4 are explored, including the following processes:

(I) Evaluation of Stress, Strain, and Load on the Myocardial Infarction Portion:

The experiment selected male rats with about 9 weeks old and about 230 g, divided into a sham group, an MI group and a patch group, with 5 rats in each group. Sham: sham operation group; MI: using a shaver to shave off the chest hair of healthy rats, injecting 1% pentobarbital anesthetic for anesthesia, fixing the four limbs of the rat on the wooden board, and connecting the ventilator to the rat's mouth, then cutting the chest skin of the rat, using a 6-0 band suture needle to ligate the coronary artery of the rat, which made the heart ischemic and hypoxic and caused myocardial infarction; Patch: to make the infarction the same as the MI group, after myocardial infarction immediately suturing the polyurethane film with a diameter of 8 mm (the thickness is 0.4 mm). The rats in three groups were sutured after surgery and then cultured for 7 days to observe the effects.

The 15 rats were taken after 7 days, turn on the universal mechanical testing machine and replace to a stretching clamp, then open the Bluehill software and clamp the hook on the fixture, so that the upper hook and the lower hook are vertical and aligned in the vertical plane. Use a shaver to shave off the chest hair of rats, inject 1% pentobarbital anesthetic for anesthesia, fix the four limbs of the rat to the wooden board, then cut the chest skin of the rat, cut off the artery connected to the heart, take it out and clean it in the Ringer's solution. Cut from the left ventricle of the heart by using scissors, spread into a rectangular plane, flatten and clamp the heart to the upper and lower hooks; adjust the position of the clamps so that the heart is just stretched, measure the length (the distance between the two hooks and the contact point of the heart), the width, and the thickness of the heart at this time by using a vernier caliper, and input into the test method of Bluehill software, set the strain produced by stretching to 30% and the strain will be completed within 1 second, then start the tensile experiment, save and export the experiment results.

The calculation results show that the stress, strain, and load of healthy myocardium are 4.890 kPa, 8.73%, and 0.00734 kgf respectively, those of the myocardial infarction part are 18.400 kPa, 10.51%, and 0.0223 kgf respectively, those of the myocardial infarction part after suturing the patch are 9.707 kPa, 5.55%, and 0.0125 kgf respectively.

Comparing the stress and strain of healthy myocardium and the myocardium of rats with myocardial infarction before and after stretching, it can be found that the strain of the myocardial infarction increases significantly after myocardial infarction, and bears a greater load, which is due to the hardening of the ventricular wall caused by myocardial fibrosis after myocardial infarction. Compared with myocardium after myocardial infarction without a patch, the stress, the strain, and the load of the myocardial infarction part after suturing the patch are significantly reduced, proving that the suture patch can provide certain mechanical support, slow down the strain increase of myocardial infarction, and make myocardial infarction part load with less burden.

Compared to myocardium after myocardial infarction without a patch, the stress, strain, and load of the myocardial infarction part with a patch are significantly reduced.

Similarly, applying the cardiac patch prepared in Examples 1-4 to the said myocardial infarction part of the heart, the experimental results showed that compared with myocardium after myocardial infarction without a patch, the stress, strain, and load of the myocardial infarction part attached by the suture-free coagulation-assisted fixed cardiac patch are significantly reduced, proving that the cardiac patch can provide certain mechanical support, slow down the strain increase of myocardial infarction, and make myocardial infarction part less loaded.

(II) Testing Process of Fixed Performance:

The experiment selected male rats with about 9 weeks old and weighing about 230 g, used a shaver to shave off the chest hair of healthy rats, injected 1% pentobarbital anesthetic for anesthesia, fixed the four limbs of the rat on the wooden board, and connected the ventilator to the rat's mouth, then cut the chest skin of the rat, used a 6-0 band suture needle to ligate the coronary artery of the rat, which made the heart ischemic and hypoxic and caused myocardial infarction; attach the cardiac patch prepared in Examples 1-4 to the myocardial infarction part of the beating heart of rats with tweezers, insert one by one and try to pull out; suture the chest skin of the rat after confirming that it was firm, culture for 7 days then check the fixation of the cardiac patch. The experimental results show that the cardiac patch can be inserted into the myocardium of living rats with myocardial infarction, and all microneedles can be inserted, the coagulation effect of the micropores is obvious; the self-locking effect is good when pulling out, which requires at least 1 N force; after the patch is implanted into the rats for 7 days, the results show that the patch can be very firmly combined with the myocardium.

(III) Testing Process of Cardiac Function:

Set three groups of rats as MI group, MI+ microneedle patch group without micropores, MI+ microneedle patch group with micropores, with 6 rats in each group, three groups of rats performed ultrasonic examination on 28 days after myocardial infarction, and dynamically observed the cardiac function change of the rats. Among them, the microneedle patch with micropores is the cardiac patch prepared in Example 2, and the difference between the microneedle patch without micropores and the cardiac patch prepared in Example 2 is only that there is no microporous structure on its surface;

The isoflurane is used for inhalation anesthesia, the precordial skin was prepared, a small animal ultrasound system was used to perform a cardiac ultrasound detection (VAVO2100, VisualSonics, Canada) on the left ventricular function of rats, with a probe frequency is 21 MHz. The probe was adjusted to obtain a clear M-type echocardiogram and a left long-axis 2D image. The average value of the left ventricular ejection fraction (LVEF) of the three groups of rats was calculated to be 49.33%, 54.70%, and 61.20%.

Comparing the data of the three groups, the MI group has no therapeutic effect; compared with the MI group, the left ventricular ejection fraction (LVEF) after the microneedle patch implantation is significantly increased, and the left ventricular systolic function is significantly improved. The left ventricular ejection fraction (LVEF) after implantation of the microneedle patch with micropores is the highest, the left ventricular systolic function is the most improved, and the therapeutic effect is the best.

What is claimed is:

1. A method of fabricating a suture-free coagulation-assisted fixed cardiac patch, comprising the following steps:
   (1) printing a first model by 3D printing, wherein the first model comprises a base, with several columns and spherical concave structures formed on a side surface of the base, and the several columns are perpendicular to the side surface;
   (2) fixing the first model horizontally in a container with the several columns facing upwards, and pouring a polydimethylsiloxane solution into the container to completely cover the first model, removing bubbles, then heating and curing to obtain a second mold;
   wherein the second mold has column hole structures and spherical protrusion structures, the column hole structures being formed by the several columns on the first model, and the spherical protrusion structures being formed by the spherical concave structures on the first model;
   (3) first, inserting a barbed microneedle dipped in a high-temperature paraffin into a column hole of the second mold, wherein a barb direction is opposite to an insertion direction, and the barbed microneedle corresponds to the column hole one by one; then casting a first solution on the second mold arranged with a microneedle array and located on a side pointed by the barb direction; finally, after a solvent in the first solution is completely volatilized, removing the second mold, a paraffin, and excess barbed microneedles; wherein a solid structure is formed during a volatilization;
   wherein the first solution is obtained by dissolving a polymer used to form a polymeric procoagulant base in a hexafluoroisopropanol solution or a dioxane solution;
   wherein the suture-free coagulation-assisted fixed cardiac patch comprises the polymeric procoagulant base and the barbed microneedle fixed on the polymeric procoagulant base, and a side surface of the polymeric procoagulant base with the barbed microneedle has a microporous structure not penetrating a solid base of the polymer;
   wherein the barbed microneedle is a microneedle with barbs and biocompatibility, an included angle α between the microneedle and a plane where the polymeric procoagulant base located is 60-90°, and microneedles are evenly distributed on the polymeric procoagulant base with a density of 5-50 threads/cm$^2$;

wherein the barbs are located on a curved surface of the microneedle and inclined toward the polymeric procoagulant base;

wherein a material of the polymeric procoagulant base is more than one selected from polyurethane, silicone rubber, polyurethane-polyurea, and polylactic acid-polycaprolactone.

2. The method of fabricating the suture-free coagulation-assisted fixed cardiac patch according to claim 1, wherein a cross-sectional shape of each of the barbs is triangular or square.

3. The method of fabricating the suture-free coagulation-assisted fixed cardiac patch according to claim 1, wherein 3-6 groups of the barbs are distributed along a longitudinal direction of the microneedle, each group consisting of 2-4 barbs, and from a cross-section of the barbed microneedle, each barb in each group of the barbs is equidistantly located on a circumference of the cross-section;

wherein an included angle between the barb and the microneedle is greater than 0° and less than or equal to 90°.

4. The method of fabricating the suture-free coagulation-assisted fixed cardiac patch according to claim 1, wherein a first end of the microneedle is a beveled needle tip, a second end of the microneedle is a flat surface, and an end of the flat surface is fixedly bonded to the polymeric procoagulant base; wherein an included angle between a bevel of the beveled needle tip and an axial direction of the microneedle is 5-45°.

5. The method of fabricating the suture-free coagulation-assisted fixed cardiac patch according to claim 1, wherein a length of the microneedle is 1-5 mm; wherein a material of the barbed microneedle is more than one selected from polylactic acid, polycaprolactone, PDO, polyethylene, and polypropylene.

6. The method of fabricating the suture-free coagulation-assisted fixed cardiac patch according to claim 1, wherein an average pore diameter of the microporous structure is 50-200 μm, an average depth of micropores is 20-120 mm, and a density of the micropores is 25-400/mm$^2$.

* * * * *